(12) United States Patent
Klocke et al.

(10) Patent No.: US 10,363,221 B2
(45) Date of Patent: Jul. 30, 2019

(54) MANUFACTURING SOLID PHARMACEUTICAL DOSAGE FORMS WITH VISIBLE MICRO- AND NANOSTRUCTURED SURFACES AND MICRO- AND NANOSTRUCTURED PHARMACEUTICAL DOSAGE FORM

(75) Inventors: Stefan Klocke, Karlsruhe (DE); Harald Walter, Zurich (CH); Alexander Stuck, Wettingen (CH)

(73) Assignee: I-Property Holding Corp., Sarasota, FL (US)

( * ) Notice: Subject to any disclaimer, the term of this patent is extended or adjusted under 35 U.S.C. 154(b) by 1448 days.

(21) Appl. No.: 12/761,993

(22) Filed: Apr. 16, 2010

(65) Prior Publication Data

US 2011/0256219 A1 Oct. 20, 2011
US 2014/0255482 A9 Sep. 11, 2014

Related U.S. Application Data

(63) Continuation of application No. PCT/US2008/011889, filed on Oct. 17, 2008.

(60) Provisional application No. 61/105,833, filed on Oct. 16, 2008, provisional application No. 60/980,665, filed on Oct. 17, 2007.

(51) Int. Cl.
*A61K 9/20* (2006.01)
*A61J 3/00* (2006.01)

(52) U.S. Cl.
CPC ............. *A61K 9/2072* (2013.01); *A61J 3/007* (2013.01)

(58) Field of Classification Search
CPC ............................... A61K 9/2072; A61J 3/007
See application file for complete search history.

(56) References Cited

U.S. PATENT DOCUMENTS

| 2,444,282 | A | * | 6/1948 | Creevy | ............... B30B 15/0011 |
| | | | | | 106/38.22 |
| 3,125,490 | A | | 3/1964 | Hershberg | |
| 3,534,440 | A | | 10/1970 | Roberts | |
| 4,668,523 | A | | 5/1987 | Begleiter | |
| 2006/0068006 | A1 | * | 3/2006 | Begleiter | ...................... 424/464 |
| 2007/0110807 | A1 | * | 5/2007 | Vergnault | ............. A61K 9/2813 |
| | | | | | 424/472 |
| 2007/0286811 | A1 | * | 12/2007 | Walter | ......................... 424/10.2 |
| 2008/0057312 | A1 | | 3/2008 | Walter et al. | |

FOREIGN PATENT DOCUMENTS

| GB | 2 343 862 A | 5/2000 |
| WO | 0110464 | 2/2001 |
| WO | 2006/027688 A1 | 3/2006 |
| WO | 2006047695 | 5/2006 |

OTHER PUBLICATIONS

McCormick, Pharmaceutical Technology, Apr. 2005, 52-62.*
International Search Report Forms: PCT/ISA/220, PCT/ISA/210, PCT/ISA/237, dated Feb. 10, 2009.

* cited by examiner

*Primary Examiner* — Robert S Cabral
(74) *Attorney, Agent, or Firm* — Wood Herron & Evans LLP

(57) ABSTRACT

A solid pharmaceutical dosage form has micro- or nanostructures impressed on the surface thereof or an interface thereof. The dosage form includes a suitable quantity and distribution of ingredients, such as one or more dyes, so as to enhance the optical contrast effect caused by the micro- or nanostructures so that the micro- or nanostructures are observable by the human eye and thereby able to provide anti-counterfeiting characteristics to the dosage form.

15 Claims, 2 Drawing Sheets

MANUFACTURING SOLID PHARMACEUTICAL DOSAGE FORMS WITH VISIBLE MICRO- AND NANOSTRUCTURED SURFACES AND MICRO- AND NANOSTRUCTURED PHARMACEUTICAL DOSAGE FORM

This application claims priority, under Section 371 and/or as a continuation under Section 120, to PCT Application No. PCT/US2008/011889, filed on Oct. 17, 2008, which claims priority to U.S. Provisional Patent Application No. 61/105,833, filed on Oct. 16, 2008, and also to U.S. Provisional Patent Application No. 60/980,665, filed on Oct. 17, 2007.

FIELD OF THE INVENTION

This invention relates to composite dosage forms such as pharmaceutical compositions and components thereof. More particularly, this invention relates to composite dosage forms comprising one or more features that provide anti-counterfeiting characteristics to such dosage forms.

BACKGROUND OF THE INVENTION

Forged, grey market, and illegal re-imports are of increasing concern in the pharmaceutical industry. This is not only a topic in the third world, where the fraction of counterfeit pharmaceutical products in the supply chain is sometimes above 50%. This problem has now reached the second and first worlds likewise, especially as pharmaceuticals are often much more expensive in these countries. AIDS and cancer drugs are sometimes subsidized in developing countries, which increases the danger of illegal re-imports.

Anti-counterfeiting strategies currently in use in the pharmaceutical industry have so far not been very successful in preventing forgery, illegal re-imports and other activities commonly summarized as counterfeiting. Anti-counterfeiting features in the pharmaceutical market nowadays are generally only applied to packages. Holograms, optically variable inks, fluorescent dyes, special printing techniques like micro-printing, and other security features are attached to the packages by use of adhesive tags, or these are laminated to the carton, or they are directly applied to the packages. The main drawback of such labels is that they can be removed from the product or the packaging and reused or analyzed. Some companies offer security features applied to the sealing foil of blister packages, but these features possess the same disadvantages.

No secure labeling of the pharmaceutical material itself, e.g., of solid dosage forms such as pills, is in the market yet. Techniques that use forgery-resistant signatures, such as DNA of known sequence (U.S. Pat. No. 5,451,505) or molecules with characteristic isotopic composition or microparticles with characteristic color layer sequence (U.S. Pat. No. 6,455,157 B1) are not applicable, as these signatures incorporate biologically active components that are consumed with the pharmaceutical material. Certification authorities, such as the Food and Drug Administration (FDA) in the U.S., have not granted approval for such anti-counterfeiting solutions.

One significant opportunity in designing pharmaceutical dosage forms is that of product identification and differentiation. It is useful, both from a consumer safety perspective and from a commercial perspective, to have a pharmaceutical dosage form with a unique appearance that is readily recognizable and identifiable.

One currently used technique for providing unique dosage form identification includes the use of intagliations. Intagliations are impressed marks typically achieved by engraving or impressing a graphical representation, for example a figure, mark, character, symbol such as a letter, a name, a logo, a pictoral representation, and the like, or any combination thereof, in a tablet or other solid dosage form, such as by a punching procedure. U.S. Pat. No. 5,827,535, for example, describes soft gelatin capsules with an external surface having defined thereon an impressed graphical representation. U.S. Pat. No. 5,405,642 discloses a method of highlighting intagliations in white or color-coated tablets by spraying onto said tablets a suspension comprising a filling material having a different color, a waxy material and a solvent, then removing the solvent and the excess filling and waxy material. However, it is often difficult to maintain the waxy material in an amount sufficient to promote suitable bonding of the filling material, yet be suitably removable with solvent.

EP 088,556 relates to a method of highlighting intagliations in white or colored tablets by contacting said tablets with a dry, powdery material having a different color than that of the tablet surface, then removing the excess powdery material not deposited in the intagliations. Disadvantageously, it has been found that the adhesion of the powdery material to the intagliations is not satisfactory, as the material shows a tendency to loosen and fall out.

EP 060,023 discloses a method of emphasizing intagliations in colored (i.e., not white) solid articles, in particular tablets, by coating the tablet surface and filling up the intagliations with a coating film comprising an optically anisotropic substance. An optical contrast between the tablet surface and the intagliations is obtained, presumably due to different orientation of the optically anisotropic substance on the tablet surface and in the intagliations. However, this technique is limited to colored articles and only allows for the use of optically anisotropic filling materials.

Another way to identify and differentiate one dosage form from another is via application of microreliefs to the dosage form. A microrelief is a regular pattern of ridges and grooves and the like that may display a visual effect or optical information when exposed to suitable light. A few ideas of applying a microrelief or hologram to edible products have been published. One is based on coating an edible product with a thermo-formable and thus embossable layer (WO 01/10464 A1). As this layer alters the composition of the product, as well as the production process, a new approval of the drug from certification authorities would be needed. Further the heating during the thereto-forming steps can harm many active agents. In another approach a polymer solution is brought into contact with a diffraction relief mold and then hardened upon drying (U.S. Pat. No. 4,668,523). The drying step can be accelerated by heating, and in the end the hardened edible polymer product possesses the diffractive relief of the mold. This method is limited to polymer solutions, it is very slow, and the heating step can be harmful to active agents used in pharmaceutical products, as it may negatively affect the activity of the active pharmaceutical agents. Disadvantageously, production difficulties could be encountered when using these methods to stamp microrelief patterns into tablets having irregular shapes and/or surfaces.

WO 2006/047695 shows a variety of methods to manufacture pharmaceutical dosage forms showing different kinds of microreliefs embedded into their surface. However, based on further review, it seems that the solutions proposed by WO 2006/047695 result in microreliefs that are not recognizable by the human eye. In particular, overcoating of microstructures usually makes them invisible because most overcoatings have a similar optical index of refraction as the pharmaceutical dosage form completely eliminating optical reflections from the interface between the two.

Other documents describing dosage forms with diffractive microstructures are WO2006027688A1, US2007/028681 A1 and WO2007144826A2. None of these documents discloses a way to enhance the color contrast between the diffractive color effects and the background of the dosage form.

SUMMARY OF THE INVENTION

The present invention relates to the manufacturing of micro- and nanostructures in pharmaceutical dosage forms by direct compression under production conditions. In particular the invention describes how geometrical structures embossed into pharmaceutical dosage forms at high speed by direct compression give rise to visible and/or measurable optical contrast in the pill by locally changing the directional optical reflectivity and/or the absorption of the surface. This contrast is useful for branding and brand protection purposes, as well as for anti-counterfeiting. In more detail this invention relates to pharmaceutical dosage forms incorporating dyes to enhance the contrast of visible and/or measureable effects based on micro- and nanostructures impressed in such forms during the direct compression process. The applicant found that only dry-compression techniques using certain pressure parameters can be employed in order to reliably obtain microreliefs in pharmaceutical dosage forms. In addition, the use of certain dyes is necessary, as the resulting colors strongly increase the human perception of the optical microstructures.

Human perception is very sensitive to contrast, not absolute intensities. A diffractive hologram on a diffuse white surface is not well visible for a human being, even if the measured diffraction efficiency of the hologram is very high. This is because the human eye not only perceives the light reflected from the hologram but also the intense light from the white surface surrounding it. The human being is "blinded" by the diffuse white surface. However, if the same hologram is on a darker background (black, dark blue, green or red for example) the rainbow colors of the hologram can be clearly seen even if the hologram is not very good. This is but one example how color and texture of a surface influence human perception.

These and other features of the invention will be more readily understood in view of the following detailed description and the drawings.

DETAILED DESCRIPTION OF THE PREFERRED EMBODIMENT

Figure 1A:
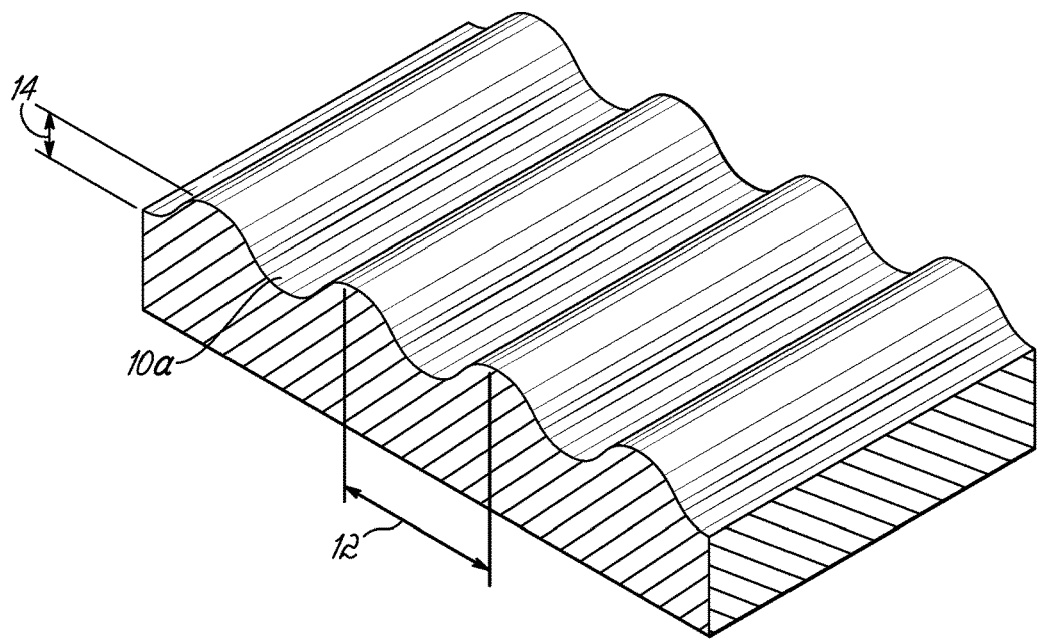
FIGS. 1A and 1B are perspective views which schematically show two types of micro- and nanostructures, according to the invention.
Figure 1B:
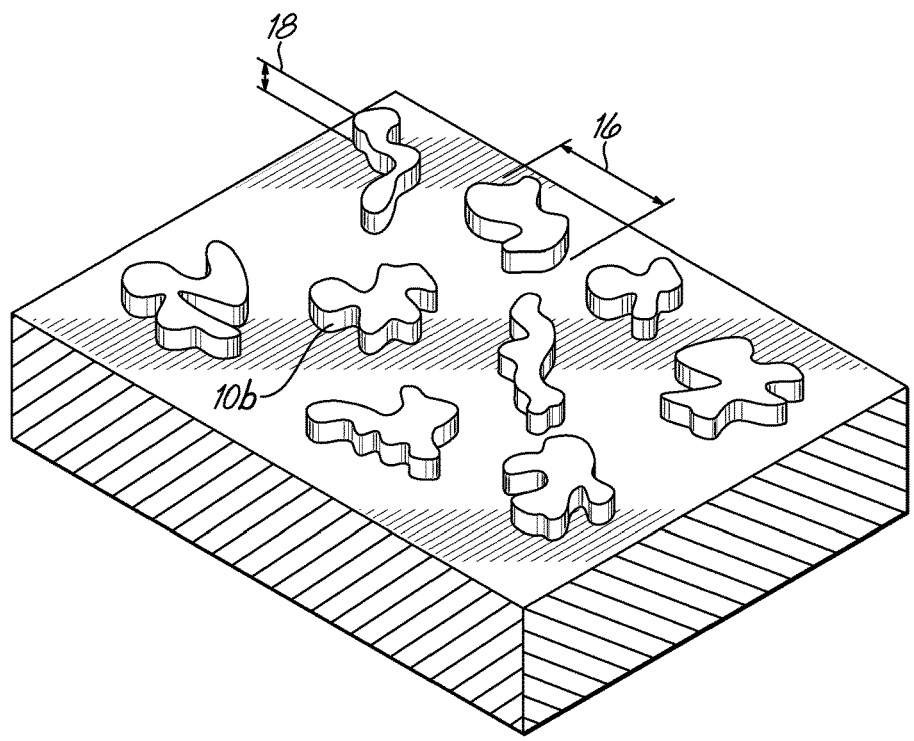

The present invention describes how well visible optical contrast in pharmaceutical dosage forms is achieved in a very fast, single manufacturing step by direct compression of suitable materials. A punching tool with a micro- and/or nanostructured surface directly compresses a pharmaceutical formulation in a press. Under the proper manufacturing conditions a very fast transfer of the tool surface geometry into the surface of the pharmaceutical dosage form is achieved. In combination with the inherent reflection and absorption properties (color) of the form material the modified surface geometry changes the local optical appearance of the surface, creating a well visible optical contrast. Depending on the precise surface geometry a single or a combination of several optical mechanisms are responsible for contrast formation: interference, diffraction, diffuse single and/or multiple scattering, single and/or multiple reflection and single and/or multiple absorption of visible light. As long as the microstructure is smaller or close to the resolution limit of the human eye, i.e. smaller than about 100 micrometers, only the optical effects of the microstructure, i.e. a contrast is perceived by humans. The microstructures can have a regular ordering or they can be irregular or random arranged. In the case of regular ordered microstructures, these structures are chosen to be larger than 2 µm, preferred larger than 5 µm, if a color contrast without or with low intense diffraction effects is the goal. Nevertheless the microstructure itself is not seen by the unaided eye. By locally changing the microstructure in the compression tool, the invention also allows to manufacture very complex geometrical contrast patterns in pharmaceutical dosage forms in a single manufacturing step.

In order to prepare a solid dosage form containing one or more active ingredients (such as drugs) for direct compression, it is necessary that the material to be compressed into the dosage form possess certain physical characteristics that lend themselves to processing in such a manner. Among other things, the material to be compressed must be free-flowing, must be lubricated, and importantly must possess sufficient cohesiveness to insure that the solid dosage form remains intact after compression.

In the case of tablets, the tablet is formed by pressure being applied to the material to be tabletted on a tablet press. A tablet press includes a lower punch that fits into a die from the bottom and an upper punch having a corresponding shape and dimension that enters the die cavity from the top after the tabletting material fills the die cavity. The tablet is formed by pressure applied on the lower and upper punches. The ability of the material to flow freely into the die is important in order to insure that there is a uniform filling of the die and a continuous movement of the material from the source of the material, e.g., a feeder hopper. The lubricity of the material is crucial in the preparation of the solid dosage forms because the compressed material must be readily ejected from the punch faces.

Because most drugs have none or only some of these properties, methods of tablet formulation have been developed in order to impart these desirable characteristics to the material(s) to be compressed into a solid dosage form. Typically, the material to be compressed into a solid dosage form includes one or more excipients that impart the free-flowing, lubrication, and cohesive properties to the drug(s) being formulated into a dosage form.

Lubricants are typically added to avoid the material(s) being tabletted from sticking to the punches. Commonly used lubricants include magnesium stearate and calcium stearate. Such lubricants are commonly included in the final tabletted product in amounts of less than 1% by weight.

In addition to lubricants, solid dosage forms often contain diluents. Diluents are frequently added in order to increase the bulk weight of the material to be tabletted in order to make the tablet a practical size for compression. This is often necessary where the dose of the drug is relatively small.

Another commonly used class of excipients in solid dosage forms are binders. Binders are agents that impart cohesive qualities to the powdered material(s). Commonly used binders include starch, and sugars such as sucrose, glucose, dextrose, and lactose.

Disintegrants are often included in order to ensure that the ultimately prepared compressed solid dosage form has an acceptable disintegration rate in an environment of use (such as the gastrointestinal tract). Typical disintegrants include starch derivatives and salts of carboxym ethylcellulose.

There are two general methods of preparation of the materials to be included in the solid dosage form prior to compression: (1) dry granulation and (2) wet granulation.

Dry granulation procedures may be used where one of the constituents, either the drug or the diluent, has sufficient cohesive properties to be tabletted. The method includes mixing the ingredients, slugging the ingredients, dry screening, lubricating, and finally compressing the ingredients.

The wet granulation procedure includes mixing the powders to be incorporated into the dosage from in, e.g., a twin shell blender or double-cone blender and thereafter adding solutions of a binding agent to the mixed powders to obtain solutions of a binding agent to the mixed powders to obtain a granulation. Thereafter the damp mass is screened, e.g., in a 6- or 8-mesh screen and then dried, e.g., via tray drying, the use of a fluid-bed dryer, spray-dryer, radio-frequency dryer, microwave, vacuum, or infra-red dryer.

In direct compression, the powdered material(s) to be included in the solid dosage form is compressed directly without modifying the physical nature of the material itself. The use of direct compression is limited to those situations where the drug or active ingredient has a requisite crystalline structure and physical characteristics required for formation of a pharmaceutically acceptable tablet. On the other hand, it is well known in the art to include one or more excipients that make the direct compression method applicable to drugs or active ingredients that do not possess the requisite physical properties. For solid dosage forms in which the drug itself is to be administered in a relatively high dose (e.g., the drug itself comprises a substantial portion of the total tablet weight), it is necessary that the drug itself have sufficient physical characteristics (e.g., cohesiveness) for the ingredients to be directly compressed.

In any case, applicant found that only direct compression techniques are feasible in order to reliably obtain micro-gratings in pharmaceutical dosage forms that would then also result in an optical effect being recognizable in a reliable manner for the human eye. US patent US2007/0286811A1, which is incorporated herein with reference, shows the fundamentals of the inventive manufacturing process that is reliably embedding micro-gratings or micro-structures into the surface of pharmaceutical dosage forms. The main principles of this process are provided herein, accompanied by important parameters regarding the operation of mass manufacturing tablet presses as well as examples of the dyes necessary in the composition of the pharmaceutical dosage form so that a satisfactory result, especially color contrast, is being obtained.

Most tablets or pills are manufactured by compressing a mixture of powders. An example of a typical mixture is denoted in Table I.

TABLE I

Example of compressing mass mixtures

| Fraction | Ingredients |
|---|---|
| 70-80% | Lactose Monohydrate |
| 10-25% | Microcrystalline Cellulose |
| <10% | Aerosil (colloidal silica, anhydrous), Magnesium-stearat (Mg-stearate), polyethyleneglycol, color and active agent |

Most of the volume is made of binding and filling agents like Lactose and Cellulose. Because of their at least partially plastic deformation behavior these and similar materials are suited to emboss the micro-structure in. Mg-stearate is used as a lubricant and Aerosil improves the powder flow. An FDA-approved colorant may be added. While most pharmaceutical pills are white, notable examples such as Viagra® are blue, others are red. Direct tabletting results in pills with a bright colored and scattering surface.

A high portion of plastic deformable materials in the formulation helps the formation of the micro-and nano-structure in the pill surface. For example the portion of microcrystalline cellulose or plastic binders like PVP may be enhanced or these materials could replace less plastic ones.

Pharmaceutical powder is made up of particles with different sizes. A typical size distribution may is shown in table II:

TABLE II

Typical particle size distribution in pharmaceutical formulations

| Fraction | Size |
|---|---|
| 15-25% | <75 micrometers |
| 30-50% | 75-150 micrometers |
| 15-25% | 150-250 micrometers |
| 5-15% | 250-500 micrometers |
| <2% | >500 micrometers |

Most particles have a size between 75 and 250 microns. Embossing microstructures with a size of 100 microns or less into the pill surface therefore deforms most particles themselves, i.e. the microstructure is embossed into the surface of the grains.

The powder mixture is compressed between two punches, which apply axial mechanical forces in the range of 5-40 kN, but depend on the size of the pill in question. Compression reduces the volume of the mass and at the same time increase its mechanical strength. The compression process is essentially a high-impact molding process and works at room temperature without heating. State-of-the-art single rotary presses work at high speed and produce about 30,000 to 300,000 pills per hour. This means that compression time per pill is well below 100 ms. This time is long enough to compress the raw powder material to a hard pill, but the pill is still soluble after it is ingested.

In a preferred embodiment of this invention, the pressure parameters of the tablet press are set in a way that correlates with the mixture of ingredients used in the particular pharmaceutical dosage form. However, it was found that pressure parameters generally have to be set at the upper end of the spectrum of commercially available tablet presses, good results for a flat pill with a diameter of 11 mm were obtained for compression forces between 15 and 35 kN. This resulted in pills with a hardness between 100-250 N. In certain embodiments of the invention the tablet press parameters were set in a range of between 10 and 50 kN, Optics of Micro- and Nanostructures:

When illuminated by polychromatic or white light, micro- and nano-structures (particularly diffractive gratings) show characteristic optical effects. FIGS. 1A and 2A schematically show two examples of such structures, designated 10a and 10b, respectively. Structure 10a has a sinusoidal diffraction grating (with period 12 and depth 14), and structure 10b has a random scattering microstructure with an average lateral structure dimension 16 of a few μm and structure height 18. The aspect ratio of the structures is the depth 14 (or 16) divided by the height 12 (or 18).

For example it is well known, that surface holograms show a distinctive rainbow pattern when illuminated by white light. Regular pyramidal structures, with sizes between 10 and 70 microns strongly diffuse light and give a satinated appearance. Randomly oriented structures with an average size between 10-100 microns may also show satination. Further such random microstructures can produce characteristic speckle pattern if illuminated by a coherent light source such as a laser of an LED. GB221870A describes security devices based on such random microstructures. Small, but deep patterns with sizes ranging in between 100-500 nm's reduce reflection and darken a given surface. In this case deep means deeper or comparable to the lateral size. Deep, self-organized nanostructures as are commonly produced by self-masking in reactive ion etching may even lead to a blackening of a surface. These and similar effects may be locally combined on their respective geometrical scales. For example a satinated pyramidal structure may be superposed with a random antireflective nanostructure to darken the satinated region. Similarly, interference gratings superimposed on satinated structures will be well visible under more viewing angles than their counterparts on a flat surface. Typical micro- and nanostructure types are listed in table III:

TABLE III

Typical optical micro- and nanostuctures

| Structure type | Dominant Optical Effect | Typical forms and dimensions |
| --- | --- | --- |
| Diffractive grating | Reflection hologram, rainbow colors | Grating period: 0.5-23 microns, aspect ratio: 0.05-1, grating shape: sinusoidal, trapezoidal, square, triangular etc. |
| Large Random structure | Satination | Average lateral dimension: 5-100 microns, Aspect ratio: 0.1-1 |
| Medium random structure | Graying, diffuse scattering, speckle pattern | Average lateral dimension: 0.5-10 microns, Aspect ratio: 0.01-0.8 |
| Small random structure | Multiple absorption, antireflex, darkening | Average lateral dimension: 50 nm to 500 nm, aspect ratio: 0.1-2 |
| Large regular structures | Satination, multiple absorption | Pyramids, Squares, Sinusoids etc, Average dimensions: 10-100 Microns, Aspect ratio: 0.2-1 |

The regular structures shown in table III, such as diffractive gratings or the large regular structures can be arranged regularly in 1 or 2 dimension in different patterns. The gratings, can be one or 2-dimensional. They may also be quasi-cristalline, i.e. exhibit a 5 fold symmetry. It is also possible to have locally regular arrangements which on a scale of several 10 microns to mm is randomly arranges, i.e. like in a 2 dimensional polycrystal. Other arrangements are conceivable as well.

Multiple optical reflection on a colored micro- or nanostructured surface leads to color shifts because multiple reflection favors the most dominant reflection peak and suppresses side peaks of the reflective spectrum. This can be easily seen from the following argument: If $R(\square)$ is the reflectivity as a function of wavelength $\square$ of a smooth surface, then $R^2(\square)$ corresponds to the amount of the twice reflected light on a structured surface, $R^3(\square)$ to the amount of three times reflected light on the structured surface and so on. As R is always smaller than one, this means that the more times the light is reflected, the weaker it becomes but it also means that the reflectivities which are closer to 1 get much less attenuated by multiple reflection than the smaller reflectivities, in effect narrowing the reflection spectrum around the maximum reflectivity. If the reflectivity spectrum contains several peaks this also means that the average reflected wavelength is shifted towards the wavelength with maximal reflectivity by multiple reflection.

This effect can be precisely controlled and gives simple possibility to manufacture a 2 colored pharmaceutical pill by combining 2 or more dyes in a given formulation. For example if a blue and red dye is added to a white formulation, the resulting flat pill may be violet. However, microstructuring parts of the surface will make this part of the pill more reddish or bluish, depending on relative reflectivities, giving a 2 colored pill.

Figure 2:
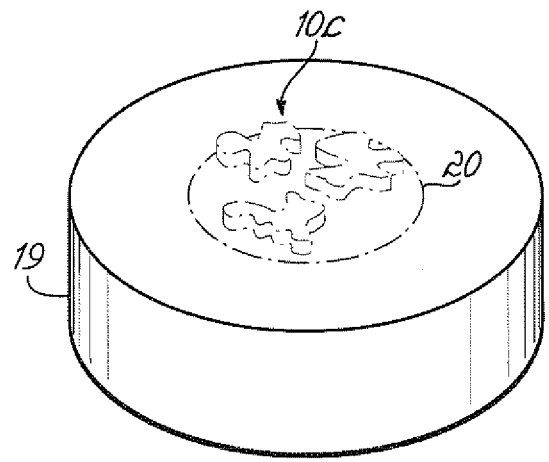
FIG. 2 is a reproduction of a photograph showing a compressed pill, with a diffractive micro-structure made by direct embossing, illuminated with white light.

It is not self-evident that micro-and nanostructures with typical lateral sizes ranging between 0.2 μm and 100 microns and aspect ratios (ration between structure depth and lateral size) between 0.1 and 2 can be reliably and stably implemented in the surface of each pill during the direct tabletting process. Considering the restrictions of this process mentioned above, it seems more or less impossible. The powders are not designed to be micro-structured. As the size of the micro-structures is smaller than the dimension of the particles, the surface of the particle itself must be microstructured. Finally, the tabletting process is very fast making the time for the micro-structuring extremely short, i.e. less than 100 ms. Nevertheless, as shown in FIG. 2, if the micro-structure in the punch surface is adapted to the process and the dye formulation, strong color contrast can be achieved by micro- and nanostructuring of pill surfaces, as shown by the micro-structure 10c that appears on the surface of dosage form 19, within the dotted circle 20.

The micro-structured area can even be macroscopically structured to form logos, brand names, and the like. This conclusion required several findings. The material of the tool which bears the micro-structure must be very hard for a long lifetime. At the same time it must be possible to implement the micro-structure in its surface. Hardened steel, hard chromium coated steel, tungsten carbide or molybdenum carbide etc. are examples of materials used for direct tabletting. They are FDA approved and can be used for the punches or dies. Unfortunately microstructuring of these materials is not achievable with the usual holographic and lithographic techniques used for example to manufacture DVD masters or to structure semiconducting surfaces. However, these materials can be microstructured using advanced non-standard etching and/or ablation techniques.

Release between tool and pill is made more difficult by the microstructures, as the contact area between the punch and the compressed pill is enhanced. The geometry of the microstructure plays a crucial role for a good release and long tool lifetime. For example, first tests with microscopic hole patterns showed that, punching several tablets with the same tool, the holes were quickly filled with residue of pill mass, inhibiting transfer of the structure into the pills. Only the first few pills showed a transfer of the microstructure. Using linear gratings, this effect was not observed. For these reasons, structures with rounded edges, walls with positive release angle and shallow structures are preferred. However, in the case of interfering structures, such as gratings, the grating efficiency strongly depends on grating depths. Usually, for a diffraction grating to be visible, a grating depth of about 100 nm or more is necessary. Also, if a lubricant is used the micro-structure must be deeper than the thickness of the lubricant between the punch and the tablet mass.

In general, adding color to the tablets significantly enhances the visible image contrast of the microstructure perceived by the human eye. Therefore a microstructure of a colored tablet needs less depth than a comparable white tablet to induce a similar image contrast. This is a great advantage for manufacturing microstructures with the direct tabletting process, as the release of the tool is easier.

Once manufactured, the microstructure needs to be protected, otherwise it may wear off. This can be done either by geometrical arrangements or by coating of the tablet. In one preferred embodiment, the microstructures are embossed at the bottom of an intagliation in the pill surface. The walls of the intgliation geometrically protect the microstructure from abrasion. Other geometrical arrangements are conceivable which protect the microstructure geometrically from abrasion.

Visibility of Micro-structures

As mentioned earlier nearly all pharmaceutical pills manufactured by the direct tabletting process possess a bright color. This bright color produces a background that may make it difficult to recognize the optical effect of the micro-and or nanostructures. As the powders usually possess an index of refraction of about 1.5 in the visible spectral range, only a few percent of the light incident on the pill surface is diffracted or directly reflected backwards. In white pills, most of the light is scattered into all directions, an only shades of grey or weak diffractive color effects can be expected on white pills.

In most cases, use of certain dyes is necessary to obtain well visible micro-and nanostructures that are recognizable to the human eye in a reliable manner. It was found by applicant during test cycles that darker dosage forms increase the contrast and are therefore superior in terms of the reliable recognition by the human eye of a micro-grating embedded in a pharmaceutical dosage form. White, pale and transparent or semi-transparent top-coating of the dosage form can make it difficult to recognize the micro-grating, sometimes to the point where it will not be recognizable at all. Dark dyes incorporated into the dosage form are generally helpful to reliably achieve the inventive effect, namely to enhance the visible or color contrast of effects based on micro- and nanostructures. Defining the visible or color contrast C as follows give a possibility to quantify the enhancement.

$$C=|I_s-I_b|/(I_s+I_b)$$

Figure 3:
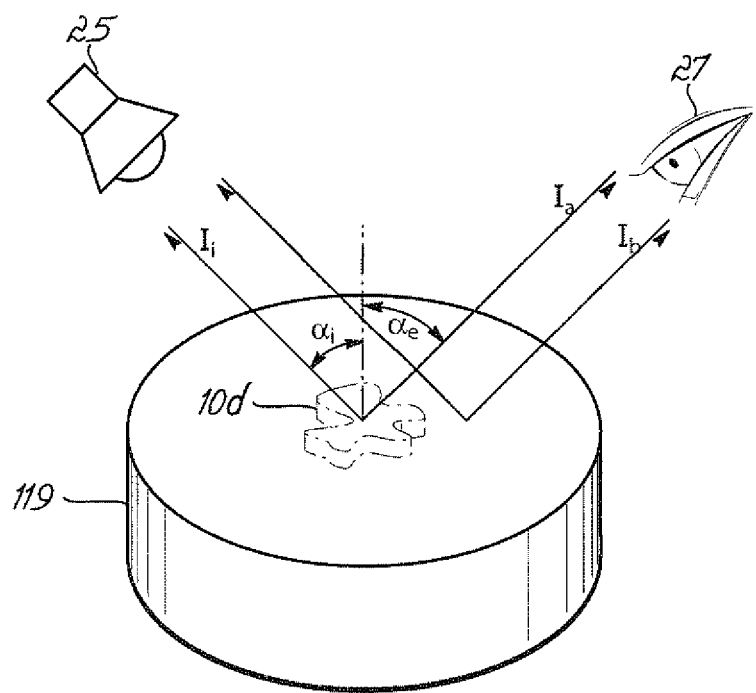
FIG. 3 is a perspective view which schematically shows the reflection/scattering/diffraction of light on a micro- and nanostructured dosage form, according to the invention.

$I_s$ and $I_b$ are the reflected light intensities from a structured part of the dosage form and an unstructured part respectively. Thus $I_b$ is the background intensity. FIG. 3 schematically depicts the reflection and/or scattering and/or diffraction of light emitted from a light source 25 toward a pharmaceutical dosage form 119, with a circular micro- and/or nanostructure 10d located in the center thereof, and eventually toward point of reference 27.

The bigger the value of C the better visible and/or measureable is the optical effect. Preferably the contrast C is >0.1, especially preferred >0.2, in particular preferred >0.4 and most preferred >0.6. The two angles $\alpha_i$ and $\alpha_e$ denote the incidence and excidence angles. They do not have to be equal. Especially for diffractive color effects both angles differ. A preferred pair of angles for the verification of diffractive micro- and nanostructures is $\alpha_i=0°$ (perpendicular illumination) and $\alpha_e=45°$.

Dyes that can be used include but are not limited to the following:
1. Naphthol Yellow SSX Spec. Pure, a nitrodye having the formula

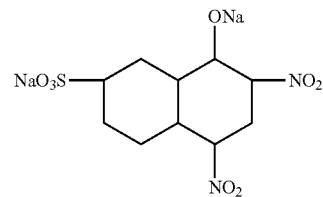

sold by Badische Anilin & Soda Fabrik, A.G., Ludwigshafen a. Rhein, Germany;
2. Orange GON Conc. Spec. Pure, a monoazo-dye having the formula

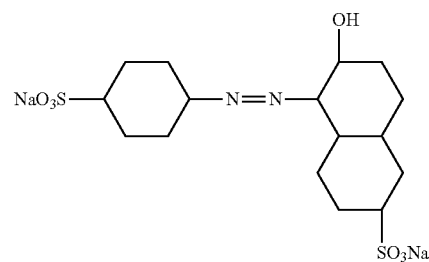

sold by Farbenfabriken Bayer A.G., Leverkusen, Germany; and Salmon Red. G.AF. a dye having the formula
sold by Farbenfabriken Bayer A.G., Leverkusen, Germany; and Salmon Red. G.AF. a dye having the formula

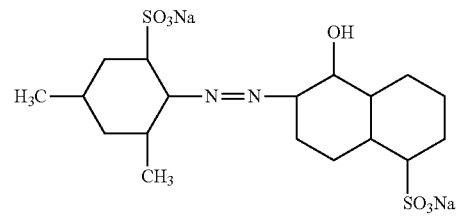

sold by CIBA Ltd., Basel, Switzerland;
3. Hexacol Chocolate Brown HT, a diazo-dye having the formula

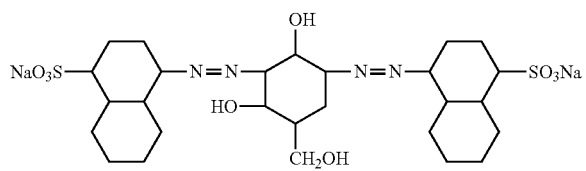

sold by L. J. Pointing & Son Ltd., Hexhem, England;

4. Heliogen Blue BIS Extra, a phthalocyanine-dye having the formula

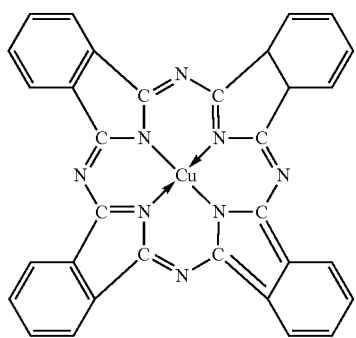

sold by General Aniline St Film Corporation, New York, N.Y.;

5. Canary Yellow Geigy, a quinoline-dye having the formula

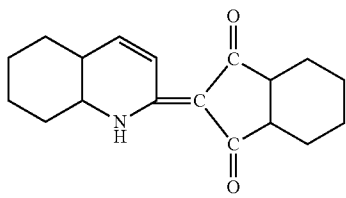 [SMILES: O=C1C(=C2C=CC3CCCCC3N2)C(=O)C2CCCCC12]

sold by J. R. Geigy S. A., Basel, Switzerland;

6. Edicol Supra Rose B, a rhodamine dye having the formula

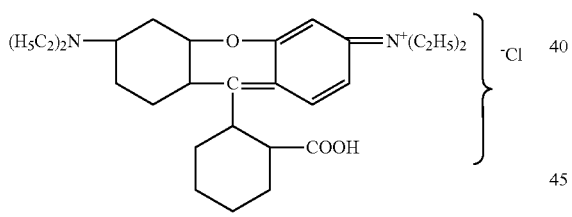

sold by Imperial Chemical Industries, Ltd., Manchester, England; and

Erythrosine TB Extra, having the formula

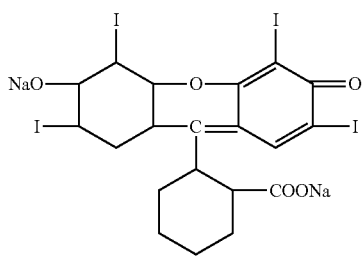

sold by Durand & Huguenin S. A., Basel, Switzerland;

7. Acid Violet 5 BN, a triaryl methane dye having the formula;

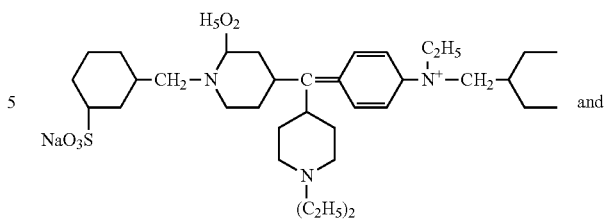

and

Acid Green S, having the formula

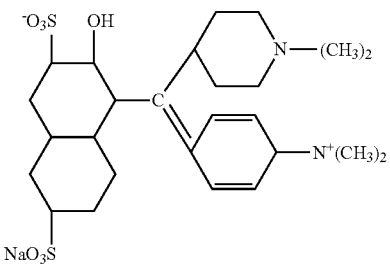

sold by Williams Ltd., Hounslow, England;

Kiton Pure Blue V. FQ, having the formula

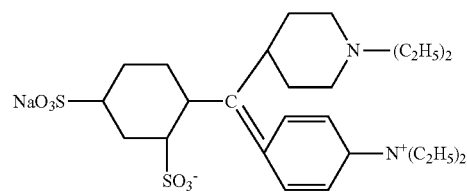

sold by Clayton Aniline Co., Ltd., Manchester, England; and

8. Edicot Supra Blue X, and indigoid dye having the formula

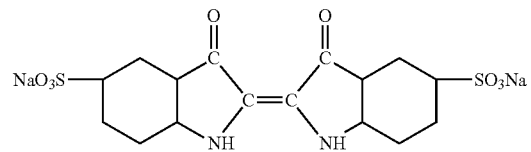

sold by Imperial Chemical Industries, Manchester, England.

Vegetable dyes, such as carotene, chlorophyll, and also tea and coffee extracts in powder form are also suitable as a dye-component. As U.S. Pat. No. 4,336,244 shows, curcumin, turmeric and annatto can be employed in the coloring of pharmaceutical dosage forms and applicant found these dyes to be suitable for the inventive purpose. Also, it is well known in the state of the art to use inert carbon or its derivatives as a component of dyes used in the manufacturing of pharmaceuticals and applicant found such dyes to be suitable for the inventive purpose.

Typically, excipients are added to the formulation to impart good flow and compression characteristics to the material as a whole that is to be compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dehydrate, among others.

A processed cellulose, microcrystalline cellulose, has been used extensively in the pharmaceutical industry as a direct compression vehicle for solid dosage forms. Microcrystalline cellulose is commercially available under the tradename, "EMCOCEL®®" from Edward Mendell. Co., Inc., and as Avicel® from FMC Corp. Compared to other directly compressible excipients, microcrystalline cellulose is generally considered to exhibit superior compressibility and disintegration properties.

Suitable polymers for inclusion in top coatings include polyvinylalcohol (PVA); water soluble polycarbohydrates such as hydroxypropyl starch, hydroxyethyl starch, pullulan, methylethyl starch, carboxymethyl starch, pre-gelantinized starches, and film-forming modified starches; water swellable cellulose derivatives such as hydroxypropyl cellulose (HPC), hydroxypropylmethyl cellulose (HPMC), methyl cellulose (MC), hydroxyethylmethyl cellulose (HEMC), hydroxybutylmethylcellulose (HBMC), hydroxyethylethylcellulose (HEEC), and hydroxyehtylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; polyvinylpyrrolidone and polyvinyl.acetate copolymers; and derivatives and combinations thereof. Suitable film-forming water insoluble polymers for inclusion in top coatings include for example ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable film-forming pH-dependent polymers for inclusion in top-coatings include enteric cellulose derivatives, such as for example hydroxypropyl methylcellulosephthalate, hydroxypropyl methylcellulose acetate succinate, cellulose acetate phthalate; natural resins, such as shellac and zein; enteric acetate derivatives such as for example polyvinylacetate phthate, cellulose acetate phthalate, acetaldehyde dimethylcellulose acetate; and enteric acrylate derivatives such as for example polymethacrylate-baserd polymers such as poly(methacrylic acid, methyl methacrylate) 1:2, which is commercially available from Rohm Pharma GmbH under the tradename, "EUDRAGIT S;" and poly(methacrylic acid, methyl methacrylate) 1:1, which is commercially available from. Rohm Pharma GmbH under the tradename "EUDRAGIT L;" poly (butyl, methacrylate (dimethylaminoethyl)methacrylate, methyl methacrylate), which is commercially available from Rohm Pharma GmbH under the tradename, "EUDRAGIT E;" and the like, and derivatives, salts, copolymers, and combinations thereof.

In one embodiment, the top coating includes coatings having a high rigidity, i.e., e.g., those coatings having a yield value sufficient to prevent deformation of the microrelief when exposed to normal manufacturing, handling, shipping, storage, and usage conditions. Suitable top coatings having high rigidity include film formers, such as for example, the high tensile strength film-formers well known in the art. Examples of suitable high tensile strength film-formers include, but are not limited to, methacrylic acid and methacrylate ester copolymers; polyvinylpyrrolidone; cellulose acetate; hydroxypropylmethylcellulose (HPMC), polyethylene oxide and polyvinylalcohol, which is commercially available from BASF under the tradename, "Kollicoat IR;" ethylcellulose; polyvinyl alcohols; and copolymers and mixtures thereof.

In one embodiment, the top coatings may include the water-soluable high rigidity fihn formers selected from HPMC, polyvinylpyrrolidone, the aminoalkyl-methacrylate copolymers marketed under the trade mark, "EUDRAGIT E;" and copolymers and mixtures thereof.

The inventive dosage form may come in a variety of different shapes. For example, in one embodiment the dosage form may be in the shape of a truncated cone. In other embodiments the dosage form may be shaped as a polyhedron, such as a cube, pyramid, prism, or the like; or may have the geometry of a space figure with some non-flat faces, such as a cone, cylinder, sphere, torus, or the like. Exemplary shapes that may be employed include tablet shapes formed from compression tooling shapes described by "the Elizabeth Companies Tablet Design Training Manual" (Elizabeth Carbide Die Co., Inc., p. 7 (McKeesport, Pa.) (incorporated herein by reference). The tablet shape corresponds inversely to the shape of the compression tooling.

In embodiments in which the dosage form is prepared via compression, suitable fillers include, but are not limited to, water-soluble compressible carbohydrates such as sugars, which include dextrose, sucrose, isomaltose, fructose, maltose, and lactose, polydextrose, sugar-alcohols, which include mannitol, sorbitol, isomalt, maltilol, xylitol, erythritol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate, and the like and mixtures thereof.

In embodiments in which the dosage form is prepared via compression, suitable binders include, but are not limited to, dry binders such as polyvinyl pyrrolidone, hydroxypropylmethylcellulose, and the like; wet binders such as water-soluble polymers, including hydrocolloids such as alginates, agar, guar gum, locust bean, carrageenan, tara, gum arabic, tragacanth, pectin, Whelan, rhamsan, zooglan, methylan, chitin, cyclodextrin, ehitosan, polyvinyl pyrrolidone, cellulosics, starches, and the like; and derivatives and mixtures thereof.

In embodiments in which the dosage form is prepared via compression, suitable disintegrants include, but are not limited to, sodium starch glycolate, cross-lined polyvinylpyrrolidone, cross-linked carboxymethylcellulose, starches, microcrystalline cellulose, and the like.

In embodiments in which the dosage form is prepared via compression, suitable lubricants include, but are not limited to, long chain fatty acids and their salts, such as magnesium stearate and stearic acid, talc, and waxes.

In embodiments in which the dosage form is prepared via compression, suitable glidants include, but are not limited to, colloidal silicon dioxide, and the like.

In embodiments in which the dosage form is prepared via compression, the dosage form of the invention may also incorporate pharmaceutically acceptable adjuvants, including but not limited to preservatives, high-intensity sweeteners such as aspartame, acesulfame potassium, cyclamate, saccharin, sucralose, and the like; and other sweeteners such as dehydroalcones, grycyrrhizin, Monellin™, stevioside, Talin™, and the like; flavors, antioxidants, surfactants, and coloring agents.

While this application describes several preferred embodiments of the invention, those skilled in the art will readily appreciate that the described embodiments are merely exemplary in nature, and that the subject matter is not limited to that which is expressly shown or described. Accordingly, applicants wish to be bound by the claims, not the particular details described herein.

We claim:

1. A method of forming a pharmaceutical dosage form comprising:
    impressing, on at least one of a surface and an interface of the dosage form, an area with at least one micro- and/or nanostructure;
    the dosage form comprising a quantity and distribution of ingredients so as to enhance an optical contrast effect caused by the impressed micro and/or nanostructure, so that the micro- and/or nanostructure is observable by the human eye,
    wherein the impressing is defined by only direct compression of a mixture of selected ingredients with a punching tool to create the solid pharmaceutical dosage form, with the direct compression performed at room temperature without heating and without modifying the physical nature of the material in the mixture, the punching tool having a micro and/or nano-structured surface formed in a tool surface geometry, and wherein particles of the mixture of selected ingredients are sized such that at least some of the particles are reconfigured or deformed by the compressing, these particles thereby taking the shape of the micro and/or nano-structured surface of the punching tool.

2. The method of claim 1, wherein at least one of the ingredients to enhance the optical contrast includes a dye.

3. The method of claim 1, wherein the optical contrast effect is greater than 0.1.

4. The method of claim 1, wherein the impressed micro- and/or nanostructure is not directly visible to the unassisted human eye, such that the unassisted human eye can only discern the optical contrast effect caused by the micro- and/or nanostructure.

5. The method of claim 4, wherein a width of the micro and/or nano-structured geometry is selected between 3 microns and 100 microns.

6. The method of claim 1, wherein the inherent reflection and absorption properties of the mixture of selected ingredients determine the optical contrast effect.

7. The method of claim 4, further comprising:
    creating the optical contrast effect via at least one of the following optical mechanisms: surface interference, diffuse single and/or multiple scattering, single and/or multiple reflection, and single and/or multiple absorption of visible light.

8. The method of claim 1, wherein the punching tool comprises a surface structure of material selected from:
    hardened steel, hard chromium coated steel, tungsten carbide, and molybdenum carbide.

9. The method of claim 1,
    wherein at least one of the following occurs:
    selecting the ingredients so as to assure flow and lubrication characteristics to enable release from the punching tool after direct compression, and
    assuring that the tool surface geometry empties after said compressing.

10. The method of claim 9, and further comprising:
    using a lubricant with the micro-structure to enhance release of the compressed pharmaceutical dosage form from the punching tool.

11. The method claim 10, wherein the micro-structure has a depth that is greater than a thickness of the lubricant and is selected between 100 and 500 microns.

12. The method of claim 1, further comprising:
    forming the tool surface geometry by at least one of the following:
    advanced etching and ablation techniques.

13. The method of claim 1, wherein the force applied via the compressing is between 35 KN and 50 KN and the hardness of the resulting dosage forms is in the range of about 100-250 N.

14. The method of claim 1, further comprising:
    adjusting pressure parameters of the compressing to correlate to the particular mixture of the ingredients.

15. The method of claim 4, further comprising:
    protecting the selected surface of the pharmaceutical dosage form that bears the optical contrast effect by at least one of the following:
    arranging the geometry of the selected surface and a coating of the dosage form.

* * * * *